United States Patent

Cho et al.

Patent Number: 5,922,727
Date of Patent: Jul. 13, 1999

[54] ANTIVIRAL SUBSTITUTED PYRIMIDINEDIONE HOMOCARBOCYCLIC NUCLEOSIDE DERIVATIVES AND METHODS FOR THE PREPARATION THEREOF AND COMPOSITIONS CONTAINING THE SAME AS ACTIVE INGREDIENTS

[75] Inventors: Eui-Hwan Cho, Seoul; Sun-Gan Chung, Kunpo; Joong-Young Kim, Suweon; Sun-Hwan Lee, Pyongtak; Ho-Seok Kwon, Suweon; Jae-Eung Lee, Hanam; Jeong-Ho Joo, Seoul; Byung-Chul Kim, Pyongtak; Dong-Wook Kang, Kwachon, all of Rep. of Korea

[73] Assignee: Samjin Pharmaceutical Co., Ltd, Seoul, Rep. of Korea

[21] Appl. No.: 08/945,121

[22] PCT Filed: Dec. 30, 1996

[86] PCT No.: PCT/KR96/00265

§ 371 Date: Jan. 21, 1998

§ 102(e) Date: Jan. 21, 1998

[87] PCT Pub. No.: WO97/30979

PCT Pub. Date: Aug. 28, 1997

[30]    Foreign Application Priority Data

Feb. 22, 1996 [KR] Rep. of Korea ............ 96-4189
Jun. 28, 1996 [KR] Rep. of Korea ............ 96-25441
Oct. 22, 1996 [KR] Rep. of Korea ............ 96-47458
Oct. 22, 1996 [KR] Rep. of Korea ............ 96-47459

[51] Int. Cl.[6] ............ A61K 31/505; C07D 239/60; C07D 239/54
[52] U.S. Cl. ............ 514/274; 544/304; 544/299; 544/314
[58] Field of Search ............ 544/309, 311, 544/314, 304, 299; 514/274

[56]    References Cited

U.S. PATENT DOCUMENTS 4,730,001  3/1988  Shealy et al. ............ 514/274
5,496,824  3/1996  Onishi et al. ............ 514/274

FOREIGN PATENT DOCUMENTS 0 420 763   4/1991  European Pat. Off. .
0 449 726  10/1991  European Pat. Off. .
93/02044    2/1993  WIPO .
95/18109    7/1995  WIPO .

Primary Examiner—Mukund J. Shah
Assistant Examiner—Ann M. Kessinger
Attorney, Agent, or Firm—Pillsbury Madison & Sutro

[57]    ABSTRACT

The present invention relates to novel compound of general formula (I) and pharmaceutically acceptable salts thereof, and process for the preparation of such derivatives and to pharmaceutical compositions containing the same as active ingredients.

General formula (I)

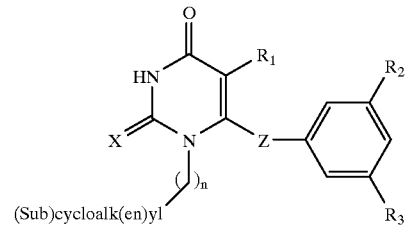

wherein $R_1$, $R_2$, and $R_3$ represents independently hydrogen atom, halogen atom, $C_1$–$C_{10}$ alkyl, $C_1$–$C_{10}$ thioalkyl, $C_3$–$C_8$ optionally substituted cyclicalkyl, unsaturated alkyl, substituted alkyl hydroxyl or aryl hydroxyl, $C_1$–$C_{10}$ alkylamine, nitro, $C_1$–$C_4$ lower ester, $C_1$–$C_4$ lower alkoxy, $C_1$–$C_4$ lower thioalkoxy; Z represents oxygen atom, sulfur atom, carbon atom and carbonyl group; X represents oxygen atom, sulfur atom; n represents an integer of 1–3; and (sub)cycloalk(en)yl represents

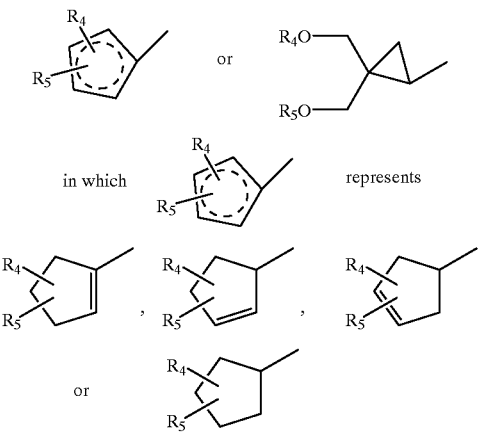

in which $R_4$ and $R_5$ represents independently hydrogen atom, hydroxymethyl, protected hydroxymethyl, benzyl, substituted carbonyl, substituted alkylsulfonyl or arylsulfonyl, substituted silyl or the like.

3 Claims, No Drawings

ANTIVIRAL SUBSTITUTED PYRIMIDINEDIONE HOMOCARBOCYCLIC NUCLEOSIDE DERIVATIVES AND METHODS FOR THE PREPARATION THEREOF AND COMPOSITIONS CONTAINING THE SAME AS ACTIVE INGREDIENTS

This application is the national phase of international application PCT/KR96/00265 filed Dec. 30, 1996 which designated the U. S.

The present invention relates, to new substituted pyrimidinedione derivatives, which are useful as an antiviral agent, treating agent for acquired immunodeficiency syndromes(AIDS), and pharmaceutically acceptable salts thereof. The invention also relates to process for the preparation of such derivatives and to pharmaceutical compositions containing the same as active ingredients.

Nowadays, various compounds such as AZT, DDC, DDI and D4T have been used as chemotherapeutic agents of AIDS and have a medical action mechanism with inhibition of the replication of AIDS virus. They also have drug tolerance and undesirable side effects due to their toxicity.
1. In order to overcome these problems, intensive researches have been carried out to develope antiviral chemotherapeutic agents with strong activity and with lower toxicity. Among them, researches have been focused on pyrimidine 6-substituted nucleoside compounds. But, N-1 substituted homocarbocyclic nucleoside derivatives were not developed as yet.

The present inventors carried out an intensive research on the N-1 substituted homocarbocyclic nucleoside derivatives and unexpectively found out the facts that the compounds have strong activity against HIV(AIDS, Acquired immunodeficiency syndromes) as well as a lower toxicity.

Accordingly, the present invention relates to new pyrimidinedione derivatives, 6-substituted pyrimidinedione homocarbocyclic nucleosides which are useful as an antiviral agent for treating acquired immunodeficiency syndromes (AIDS), and pharmaceutically acceptable salts thereof.
2. The present compounds have the following general formula(I).

General formula (I)

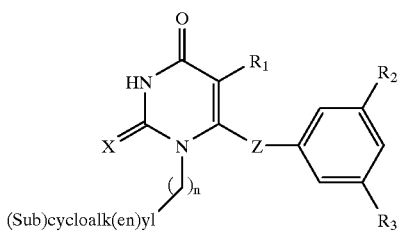

(Sub)cycloalk(en)yl wherein $R_1$, $R_2$, and $R_3$ represents independently hydrogen atom, halogen atom, $C_1$–$C_{10}$ alkyl, $C_1$–$C_{10}$ thioalkyl, $C_3$–$C_8$ optionally substituted cyclicalkyl, unsaturated alkyl, substituted alkyl hydroxyl or aryl hydroxyl, $C_1$–$C_{10}$ alkylamine, nitro, $C_1$–$C_4$ lower ester, $C_1$–$C_4$ lower alkoxy, $C_1$–$C_4$ lower thioalkoxy; Z represents oxygen atom, sulfur atom, carbon atom and carbonyl group; X represents oxygen atom, sulfur atom; n represents an integer of 1–3; and (sub)cycloalk(en)yl represents

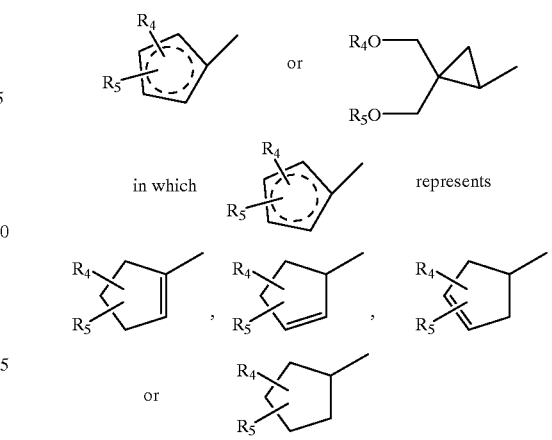

in which $R_4$ and $R_5$ represents independently hydrogen atom, hydroxymethyl, protected hydroxymethyl, benzyl, substituted carbonyl, substituted alkylsulfonyl or arylsulfonyl, substituted silyl or the like.

$C_1$–$C_{10}$ alkyl means straight or branch alkyl group such as methyl, ethyl, propyl, butyl, isobutyl, t-butyl, pentyl, isopentyl, hexyl, heptyl, octyl, 2-methyl-pentyl or the like.

$C_1$–$C_{10}$ thioalkyl means straight or branch thioalkyl group such as methylthio, ethylthio, propylthio, butylthio, isobutylthio, t-butylthio, pentylthio, isopentylthio, hexylthio, heptylthio, octylthio, 2-methyl-pentylthio or the like.

$C_3$–$C_8$ optionally substituted cyclic alkyl means cyclic propyl, cyclic butyl, cyclic pentyl, methyl cyclic propyl, methyl cyclic butyl, methyl cyclic pentyl or the like.

$C_1$–$C_4$ lower ester means a carboxylic group was esterified by lower alkyl group or the like.

$C_1$–$C_4$ lower alkoxy means methoxy, ethoxy, propyloxy, butyloxy, isobutyloxy, t-butyloxy or the like.

$C_1$–$C_4$ lower thioalkoxy means thiomethoxy, thioethoxy, thiopropyloxy, thiobutyloxy, thioisobutyloxy, thio t-butyloxy or the like.

The substituted carbonyl group means acetyl, benzoyl, substituted benzoyl or the like.

The substituted alkylsulfonyl, arylsulfonyl group means methanesulfonyl, para-toluenesulfonyl, benzenesulfonyl, para-nitrobenzenesulfonyl or the like.

The substituted silyl group means trimethylsilyl, dimethylphenylsilyl, t-butyldimethylsilyl or the like.

The present inventors had studied the active compound as an antiviral agent for long time. As a result, the present inventors unexpectively found out the facts that the compounds of the general formula(I) have excellent antiviral activity against HIV and very low toxicity.

In accordance with present invention, there are provided pharmaceutical compositions comprising one or more of the general formula(I) and their salts with a excellent antiviral activity against HIV and very low toxicity.

In accordance with still another aspect of the present invention, there are provided with processes for preparing the compounds of the general formula(I) and their salts.

The compounds of the present invention can be mixed with pharmaceutically acceptable vehicles by a known method to give pharmaceutical compositions and the pharmaceutical compositions can be used to prevent or treat various kinds of virus disease. Another object of the present invention is to provide pharmaceutical compositions containing the general formula(I) and their salts.

The acids which can be reacted with the compounds of the general formula(I) to form acid salts are pharmaceutical acceptable inorganic acids such as hydrochloric acid, hydrobromic acid, sulfuric acid. phosphoric acid, nitric acid ; organic acids such as formic acid, acetic acid, trifluoroacetic acid, propionic acid, succinic acid, citric acid, maleic acid malonic acid,; sulfonic acids such as sulfonic acid, methanesulfonic acid, ethanesulfonic acid, benzenesulfonic acid, toluenesulfonic acid; amino acids such as alanine, glycine, phenyl glycine, serin, cisserin, cystein, asparaginic acid, glutamic acid, lysine, arginine, tylosine, proline or the like. The vehicles which can be used in the preparation of pharmaceutical compositions containing the compounds of the general formula(I) as active ingredient are sweetening agent, binding agent, dissolving agent, aids for dissolution, wetting agent, emulsifying agent, isotonic agent, adsorbent, degrading agent, antioxident, antiseptics, lubricating agent, filler and perfume or the like such as lactose, dextrose, sucrose, mannitol, sorbitol, cellulose, sodium carboxy methyl cellulose, agar, talc, stearic acid, magnesium stearate, calcium stearate, magnesium aluminium silicate, starch, gelatine, tragacanth gum, methyl cellulose, glycine, silica, alginic acid, sodium alginate, water, ethanol, polyethyleneglycol, polyvinyl pyrrolidone, sodium chloride, potassium chloride, orange essence, vanilla aroma or the like.

Daily dosage of the compound of the general formula(I) may be varied depending on age, sex of patient and the degree of disease. Daily dosage is 1.0 mg to 5,000 mg and may be administered one to several times.

The compounds of the general formula(I) may be prepared by the following scheme 1.

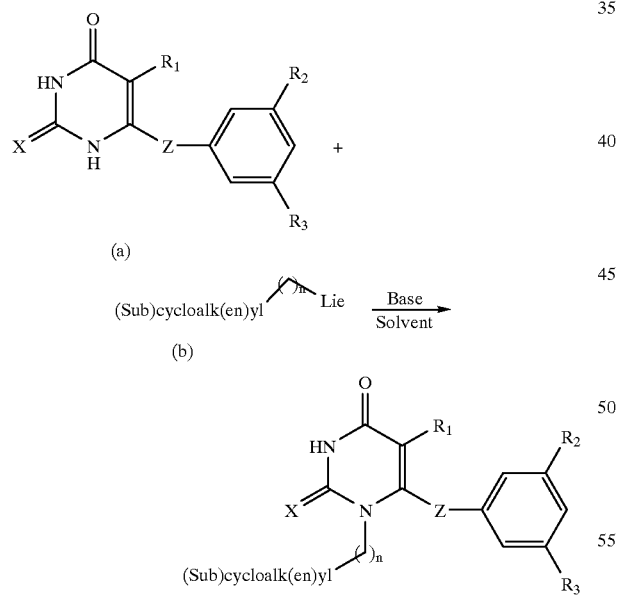

wherein (Sub)cycloalk(en)yl, $R_1$, $R_2$, $R_3$, Z, X, and n have the same meanings as defined above and Lie represents a leaving group as a halogen atom, alkylsulfonyl or arylsulfonyl group.

The compounds of the general formula(I) may be prepared by reacting a compound of the general formula(a) and the general formula(b) in the presence of a base.

Representative of the base include sodium bicarbonate, sodium carbonate, potassium carbonate, sodium hydride, potassium hydride, cesium carbonate. Representatives of the solvent include dimethylformamide, ethanol, (acetonitrile, dimethylsulfoxide or the like. The reaction may be carried out between 10° C. and 100° C. for 5–48 hrs.

The compounds of the general formula(I) may be prepared by the following scheme 2.

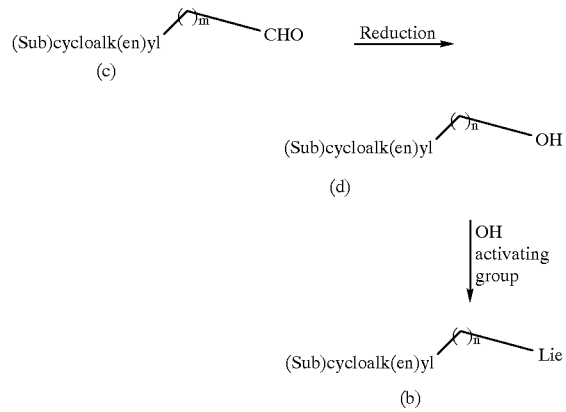

wherein n has the same meaning and m is an integer of 0–2. The representative reducing agents include sodium borohydride, lithium aluminium hydride and the activating group of hydroxy pant include halogen atom and sulfonyl group or the like. The sulfonyl group include alkylsulfonyl group such as methanesulfonyl and arylsulfonyl group such as para-toluenesulfonyl, benzenesulfonyl and para-nitrobenzenesulfonyl group. The general formula(d) can be effectively obtained by the reaction of the general formula(c) and the reduction agent. And the general formula(b) can be effectively prepared by the introduction of the activating group of the general formula(c).

The known compounds of 6-substituted pyrimidinedione derivatives(a) used in the preparation of the general formula (I) are described in prior paper(WO 93/02044, WO 95/18109) or may be prepared in a similar method to the paper.

EXAMPLES

The compounds of the general formula(I) are prepared by the following examples.

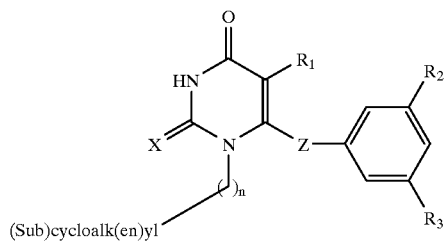

wherein $R_1$, $R_2$, $R_3$, Z, X, (Sub)cycloalk(en)yl and n have the same meanings above.

| Examples No | R₁ | R₂ | R₃ | (Sub)cyclo-alk(en)yl | X | Z | n |
|---|---|---|---|---|---|---|---|
| 1 | Et | H | H | cyclopentenyl | O | S | 1 |
| 2 | Et | Me | Me | cyclopentenyl | O | S | 1 |
| 3 | iPr | H | H | cyclopentenyl | O | S | 1 |
| 4 | iPr | Me | Me | cyclopentenyl | O | S | 1 |
| 5 | Et | H | H | cyclopentenyl | O | S | 1 |
| 6 | Et | H | H | HO-cyclopentenyl | O | S | 1 |
| 7 | Et | Me | Me | HO-cyclopentenyl | O | S | 1 |
| 8 | iPr | H | H | HO-cyclopentenyl | O | S | 1 |
| 9 | iPr | Me | Me | HO-cyclopentenyl | O | S | 1 |
| 10 | Et | H | H | cyclopentenyl-CH₂OH | O | S | 1 |
| 11 | Et | Me | Me | cyclopentenyl-CH₂OH | O | S | 1 |
| 12 | iPr | H | H | cyclopentenyl-CH₂OH | O | S | 1 |
| 13 | iPr | Me | Me | cyclopentenyl-CH₂OH | O | S | 1 |
| 14 | Et | Me | Me | cyclopentenyl | O | O | 1 |
| 15 | iPr | Me | Me | cyclopentenyl | O | O | 1 |
| 16 | Et | Me | Me | cyclopentenyl | O | C=O | 1 |
| 17 | iPr | Me | Me | cyclopentenyl | O | C=O | 1 |
| 18 | Et | Me | Me | HO-cyclopentenyl | O | O | 1 |
| 19 | Et | Me | Me | cyclopentenyl-CH₂OH | O | O | 1 |
| 20 | iPr | Me | Me | cyclopentyl | O | S | 1 |
| 21 | iPr | Me | Me | cyclopentyl | O | O | 1 |

-continued
| Examples No | R₁ | R₂ | R₃ | (Sub)cyclo-alk(en)yl | X | Z | n |
|---|---|---|---|---|---|---|---|
| 22 | iPr | Me | Me |  | O | C=O | 1 |
| 23 | Et | Me | Me |  | O | C=O | 1 |
| 24 | Et | H | H | 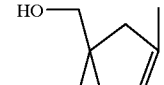 | O | S | 1 |
| 25 | Et | Me | Me | 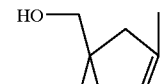 | O | S | 1 |
| 26 | iPr | H | H | 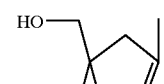 | O | S | 1 |
| 27 | iPr | Me | Me | 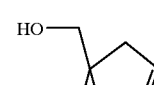 | O | S | 1 |
| 28 | Et | H | H | 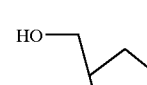 | O | S | 1 |
| 29 | Et | Me | Me | 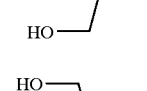 | O | S | 1 |
| 30 | iPr | Me | Me | 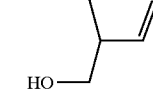 | O | S | 1 |
| 31 | Et | Me | Me | 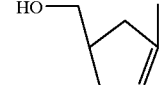 | O | O | 1 |
| 32 | iPr | Me | Me | 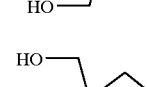 | O | O | 1 |
-continued
| Examples No | R₁ | R₂ | R₃ | (Sub)cyclo-alk(en)yl | X | Z | n |
|---|---|---|---|---|---|---|---|
| 33 | Et | Me | Me | 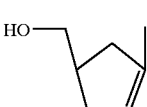 | O | C=O | 1 |
| 34 | iPr | Me | Me | 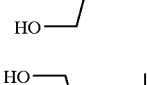 | O | C=O | 1 |
| 35 | Et | Me | Me | 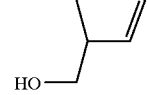 | O | C=O | 2 |
| 36 | Et | Me | Me |  | O | C=O | 2 |
| 37 | iPr | Me | Me |  | O | C=O | 2 |
| 38 | iPr | Me | Me |  | O | O | 2 |
| 39 | iPr | Me | Me |  | O | S | 2 |
| 40 | Et | Me | Me |  | O | C=O | 2 |
| 41 | iPr | Me | Me | 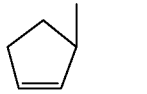 | O | C=O | 2 |
| 42 | iPr | Me | Me | 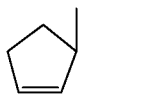 | O | O | 2 |
| 43 | iPr | Me | Me | 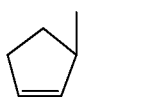 | O | S | 2 |
| 44 | Et | Me | Me |  | O | C=O | 2 |

-continued

| Examples No | R₁ | R₂ | R₃ | (Sub)cyclo-alk(en)yl | X | Z | n |
|---|---|---|---|---|---|---|---|
| 45 | iPr | Me | Me |  | O | C=O | 2 |
| 46 | iPr | Me | Me |  | O | O | 2 |
| 47 | iPr | Me | Me |  | O | S | 2 |
| 48 | Et | H | H | 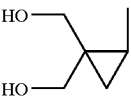 | O | S | 1 |
| 49 | Et | Me | Me | 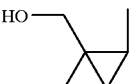 | O | S | 1 |
| 50 | Et | Me | Me | 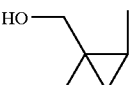 | O | O | 1 |
| 51 | Et | Me | Me | 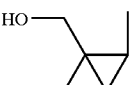 | O | C=O | 1 |
| 52 | iPr | H | H | 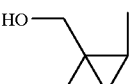 | O | S | 1 |
| 53 | iPr | Me | Me | 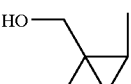 | O | S | 1 |
| 54 | iPr | Me | Me | 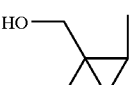 | O | O | 1 |
| 55 | iPr | Me | Me | 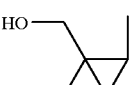 | O | C=O | 1 |

Example 1

1-[(Cyclopent-3-en-1-yl)methyl]-5-ethyl-6-phenylthio-2,4-pyrimidinedione 1-a) (Cyclopent-3-en-1-yl)methyl toluenesulfonate A mixture of (cyclopent-3-en-1-yl)methanol (1.96 g, 20 mmol) and para-toluenesulfonylchloride (3.81 g, 20 mmol) were stirred at room temperature for 2 hrs in pyridine (30 ml). After the concentration of pyridine, the reaction residues were extracted with dichloromethane, washed 1N HCl, dried with $MgSO_4$, concentrated and separated by the column chromatography to give the desirable product (4.20 g).

Yield(%): 83.2

$^1$H NMR($CDCl_3$): δ2.11(2H,m), 2.42(3H,s), 2.49(3H,m), 3.82(2H,d), 5.67(2H,s), 7.40(2H,d), 7.65(2H,d).

1-b 1-[(Cyclopent-3-en-1-yl)methyl]-5-ethyl-6-phenylthio-2,4-pyrimidinedione

A mixture of 5-ethyl-6-phenylthio-2,4-pyrimidinedione (0.10 g, 0.40 mmol) and (cyclopent-3-en-1yl)methyl toluenesulfonate (0.12 g, 0.40 mmol) in dimethylformamide (10 ml) were heated at 90° C. for overnight in the presence of sodium bicarbonate (41 mg, 0.4 mmol). After the concentration of dimethylformamide under vacuum distillation, the desirable product was obtained as white solid (65 mg) by the separation of column chromatography.

Yield(%): 49.1 m.p: 112–113° C.

$^1$H NMR($CDCl_3$): δ1.13(3H,t), 2.10(2H,m), 2.38(2H,m), 2.70(2H,q), 3.97(2H,d,J=7.65 Hz), 5.67(2H,s), 7.14–7.53 (5H,m), 8.51(1H,s).

Example 2

1-[(Cyclopent-3-en-1-yl)methyl]-5-ethyl-6-(3,5-dimethylphenylthio)-2,4-pyrimidinedione 5-ethyl-6-(3,5-dimethylphenylthio)-2,4-pyrimidinedione and (cyclo-3-en-1-yl)methyl toluenesulfonate were reacted by the same way with example 1 to obtain the titled compound.

Yield(%): 45.2 m.p: 128–130° C.

$^1$H NMR($CDCl_3$): δ1.03(3H,t), 2.10(2H,m), 2.37(2H,m), 2.68(2H,q), 2.83(1H,m), 3.99(2H,d,J=7.65 Hz), 5.68(2H,s), 6.73(2H,s), 6.88(1H,s), 8.98(1H,s).

Mass: m/e 356(M⁺), 219(100)

Example 3

1-[(Cyclopent -3-en-1-yl)methyl]-5-isopropyl-6-phenylthio-2,4-pyrimidinedione

5-Isopropyl-6-phenylthio-2,4-pyrimidinedione and (cyclopent-3-en-1-yl) methyl toluenesulfonate were reacted by the same way with example 1 to obtain the titled compound.

Yield(%): 57.6 m.p: 131–134° C.

$^1$H NMR($CDCl_3$): δ1.21(6H,d,J=6.95 Hz), 2.10(2H,m), 2.39(2H,m), 2.80(1H,m), 4.06(2H,d,J=7.65 Hz), 5.68(2H,s), 7.14–7.35(5H,m), 9.14(1H,s)

Mass: m/e 342(M⁺), 233(100)

Example 4

1-[(Cyclopent-3-en-1-yl)methyl]-5-isopropyl-6-(3,5-dimethylphenylthio) -2,4-pyrimidinedione 5-Isopropyl-6-(3,5-dimethylphenylthio)-2,4-pyrimidinedione and (cyclopent-3-en-1-yl)methyl toluenesulfonate were reacted by the same way with example 1 to obtain the titled compound.

Yield(%): 62.8 m.p: 139–141° C.

¹H NMR(CDCl₃): δ1.20(6H,d,J=6.95 Hz), 2.10(2H,m), 2.28(6H,s), 2.39(2H,m), 2.77(1H,m), 3.51(1H,m), 4.05(2H, d,J=7.65 Hz), 5.68(2H,s), 6.74(2H,s), 6.88(1H,s), 8.34(1H, s).

Mass: m/e 370(M⁺), 233(100)

Example 5

1-[(Cyclopent-1-en-1-yl)methyl]-5-ethyl-6-phenylthio-2,4-pyrimidinedione 5-a) (Cyclopent-1-en-1-yl)methyl toluenesulfonate A mixture of (cyclopent-1-en-1-yl)methanol (1.96 g, 20 mmol) and para-toluenesulfonylchloride (3.81 g, 20 mmol) were stirred at room temperature for 2 hrs in pyridine (30 ml). After the concentration of pyridine, the reaction residues were extracted with dichloromethane, washed 1N HCl, dried with MgSO₄, concentrated and separated by the column chromatography to give the desirable product (4.52 g).

Yield(%): 89.6

¹H NMR(CDCl₃): δ1.84(2H,m), 2.23(4H,s), 2.49(3H,s), 4.21(2H,s), 5.27(1H,s), 7.40(2H,d), 7.65(2H,d).

5-b) 1-[(Cyclopent-1-en-1-yl)methyl]-5-ethyl-6-phenylthio-2,4-pyrimidinedione

A mixture of 5-ethyl-6-phenylthio-2,4-pyrimidinedione (0.10 g, 0.40 mmol) and (cyclopent-3-en-1yl)methyl toluenesulfonate (0.12 g, 0.40 mmol) in dimethylformamide (10 ml) were heated at 90° C. for overnight in the presence of sodium bicarbonate (41 mg, 0.48 mmol). After the concentration of dimethylformamide under vacuum distillation, the desirable product was obtained as white solid (45 mg) by the separation of column chromatography.

Yield(%): 34.2 m.p: 181–183° C.

¹H NMR(CDCl₃): δ1.01(3H,t), 1.84(2H,m), 2.23(2H,m), 2.69(2H,q), 4.66(2H,s), 5.26(1H,s), 7.15–7.34(5H,m), 8.94 (1H,s)

Example 6

1-[(4-Hydroxymethylcyclopent-1-en-1-yl)methyl]-5-ethyl-6-phenylthio-2,4-pyrimidinedione.

6-a) (4-t-Butyldimethylsilyloxymethylcyclopent-1-en-1-yl)methyl bromide

The carbon tetrabromide (1.39 g, 4.2 mmol) and triphenylphosphine (1.37 g, 5.2 mmol) were added in dichloromethane solution of (4-t-Butyldimethylsilyloxymethylcyclopent-1-en-1-yl)methyl alcohol (0.85 g, 3.5 mmol) under ice bath and then stirred for 30 min at 0° C. The reaction mixture was stirred for overnight at room temperature, extracted with dichloromethane, dried with MgSO₄, filtered, concentrated and separated by column chromatography to give a desirable product (0.53 g).

Yield(%): 49.7

¹H NMR(CDCl₃): δ0.05(6H,s), 0.90(9H,s), 2.18(2H,m), 2.50(3H,m), 3.50(2H,d,J=6.75 Hz), 4.05(2H,s), 5.71(1H,s)

6-b) 1-[(4-Hydroxymethylcyclopent-1-en-1-yl)methyl]-5-ethyl-6-phenylthio-2,4-pyrimidinedione A mixture of 5-ethyl-6-phenylthio-2,4-pyrimidinedione (0.16 g, 0.66 mmol) and (4-t-butyldimethylsilyloxymethylcyclopent-1-en-1-yl)methyl bromide (0.20 g, 0.66 mmol) in dimethylformamide (10 mmol) were heated at 50° C. for overnight in the presence of sodium bicarbonate (66 mg, 0.79 mmol). After the concentration of dimethylformamide, [(4-t-butyldimethylsilyloxymethyl cyclopent-1-en-1-yl)methyl]-5-ethyl-6-phenylthio-2,4-pyrimidinedione was obtained by the separation of the column chromatography. And then, this compound in THF (10 ml) was reacted with n-tetrabutylammoniumfluoride at room temperature for 1 hr. After the concentration of THF, the residue was separated by column chromatography to give a desirable product (35 mg).

Yield(%): 14.8 m.p): 161–163° C.

¹H NMR(CDCl₃): δ1.01(3H,t), 2.03(2H,m), 2.38(2H,m), 2.50(1H,m), 2.68(2H,q), 3.50(2H,d,J=6.65 Hz), 5.23(1H,s), 7.15–7.35(5H,m), 8.62(1H,s).

Example 7

1-[(4-Hydroxymethylcyclopent-1-en-1-yl)methyl]-5-ethyl-6-(3,5-dimethylphenylthio)-2,4-pyrimidinedione 5-Ethyl-6-(3,5-dimethylphenylthio)-2,4-pyrimidinedione and (4-t-butyl-dimethylsilyloxymethylcyclopent-1-en-1-yl) methyl bromide were reacted by the same way with the example 6 to obtain the titled compound (48 mg).

Yield(%): 21.4 m.p: 57–60° C.

¹H NMR(CDCl₃): δ1.02(3H,t), 2.04(2H,m), 2.28(6H,s), 2.39(H,m), 2.51(1H,m), 2.68(2H,q), 3.51(2H,d,J=9.7 Hz), 4.63(2H,q), 5.23(1H,s), 6.75(2H,s), 6.87(1H,s), 9.38(1H,s).

Example 8

1-[(4-Hydroxymethylcyclopent-1-en-1-yl)methyl]-5-isopropyl-6-phenylthio-2,4-pyrimidinedione 5-Isopropyl-6-phenylthio-2,4-pyrimidinedione and [(4-t-butyldimethylsilyl-oxymethylcyclopent-1-en-1-yl)methyl bromide were reacted by the same way with the example 6 to obtain the titled compound (67 mg)

Yield(%): 29.5 m.p: 166–168° C.

¹H NMR(CDCl₃): δ1.18(3H,d), 1.19(3H,d), 2.05(2H,m), 2.41(2H,m), 2.50(1H,m), 3.49(1H,m), 3.52(2H,d), 4.70(2H, q), 5.24(1H,s), 7.16–7.34(5H,m), 8.63(1H,s).

Example 9

1-[(4-Hydroxymethylcyclopent-1-en-1-yl)methyl]-5-isopropyl-6-(3,5-di-methylphenylthio)- 2,4-pyrimidinedione 5-Isopropyl-6-(3,5-dimethylphenylthio)-2,4-pyrimidinedione and (4-t-butyldimethylsilyloxymethylcyclopent-1-en-1-yl)methyl bromide were reacted by the same way with the example 6 to obtain the titled compound (73 mg)

Yield(%): 33.1 m.p: 147–148° C.

¹H NMR(CDCl₃): δ1.20(3H,d), 1.21(3H,d), 2.05(2H,m), 2.28(6H,s), 2.40(2H,d), 2.59(1H,m), 3.49(1H,m), 3.52(2H, d,J=6.85 Hz), 4.70(2H,q), 5.24(1H,s), 6.75(2H,s), 6.87(1H, s), 9.06(1H,s)

Mass: m/e 400(M⁺), 263(100)

Example 10

1-[(5-Hydroxymethylcyclopent-1-en-1-yl)methyl]-5-ethyl-6-phenylthio-2,4-pyrimidinedione 10-a) (5-t-butyldimethylsilyloxymethylcyclopent-1-en-1-yl)methyl bromide The carbon tetrabromide (8.5 g, 25.7 mmol) and triphenylphosphine (8.4 g, 3.22 mmol) were added in dichloromethane solution of (5-t-Butyldimethylsilyloxymethylcyclopent-1-en-1-yl)methyl alcohol (5.2 g, 21.4 mmol) under ice bath and then stirred for 30 min at 0° C. The reaction mixture was stirred for overnight at room temperature, extracted with dichloromethane, dried with MgSO$_4$, filtered, concentrated and separated by column chromatography to give a desirable product (3.08 g).

Yield(%): 47.2

$^1$H NMR(CDCl$_3$): δ0.05(6H,s). 0.90(9H,s), 1.71(2H,m), 2.05(2H,m), 2.30(2H,m), 3.62(2H,d,J=5.8 Hz), 4.15(2H,s), 5.71(1H,s).

10-b) 1-[(5-Hydroxymethylcyclopent-1-en-1-yl)methyl]-5-ethyl-6-phenylthio-2,4-pyrimidinedione A mixture of 5-ethyl-6-phenylthio-2,4-pyrimidinedione (0.16 g, 0.66 mmol) and (5-t-butyldimethylsilyloxymethylcyclopent-1-en-1-yl)methyl bromide (0.20 g, 0.66 mmol) in dimethylformamide (10 ml) were heated at 50° C. for overnight in the presence of sodium bicarbonate (66 mg, 0.79 mmol). After the concentration of dimethylformamide, [(5-t-butyldimethylsilyloxymethyl cyclopent-1-en-1-yl)methyl]-5-ethyl-6-phenylthio-2,4-pyrimidinedione was obtained by the separation of the column chromatography. And then, this compound in THF (10 ml) was reacted with n-tetrabutylammoniumfluoride at room temperature for 1 hr. After the concentration of THF, the residue was separated by column chromatography to give a desirable product (35 mg).

Yield(%): 18.2 m.p: 155–156° C.

$^1$H NMR(CDCl$_3$): δ1.04(3H,t), 1.81–1.90(4H,m), 2.72 (3H,m), 3.56–3.7 (2H,dd,J=4.35 Hz), 4.70(2H,dd,J=16.9 Hz) 5.32(1H,s), 7.17–7.36(5H,m), 9.90(1H,s).

Example 11

1-[(5-Hydroxymethylcyclopent-1-en-1-yl) methyl]-5-ethyl-6-(3,5-dimethylphenylthio)-2,4-pyrimidinedione 5-Ethyl-6-(3,5-dimethylphenylthio)-2,4-pyrimidinedione and (5-t-butyldimethylsilyloxymethylcyclopent-1-en-1-yl) methyl bromide were reacted by the same with the example 10 to obtain the titled compound.

Yield(%): 22.7 m.p: 59–60° C.

$^1$H NMR(CDCl$_3$): δ1.05(3H,t), 1.83–2.27(4H,m), 2.28 (6H,s), 2.73(3H,m), 3.57–3.74(2H,dd,J=4.30 Hz), 4.60(2H, dd,J=17 Hz), 5.31 (1H,s), 6.77(2H,s), 6.88(1H,s), 9.39(1H, s).

Example 12

1-[(5-Hydroxymethylcyclopent-1-en-1-yl)methyl]-5-isopropyl-6-(3,5-dimethylphenylthio)-2,4-pyrimidinedione 5-Isopropyl-6-(3,5-dimethylphenylthio)-2,4-pyrimidinedione and (5-t-butyldimethylsilyloxymethylcyclopent-1-en-1-yl)methyl bromide were reacted by the same with the example 10 to obtain the titled compound. (68 mg)

Yield(%): 29.9 m.p: 66–68° C.

$^1$H NMR(CDCl$_3$): δ1.21(3H,d,J=7.0 Hz), 1.24(3H,d,J= 7.0 Hz), 1.81–2.34(4H,m), 2.73(1H,m), 3.51(1H,m), 3.57–3.74(2H,dd,J=4.45 Hz), 4.66(2H,dd,J=17.0 Hz),

Example 13

1-[(5-Hydroxymethylcyclopent-1-en-1-yl)methyl]-5-Isopropyl-6-(3,5-dimethyl-phenylthio)-2,4-pyrimidinedione 5-Isopropyl-6-(3,5-dimethylphenylthio)-2,4-pyrimidinedione and (5-t-butyldimethylsilyloxymethylcyclopent-1-en-1-yl)methyl bromide were reacted by the same with the example 10 to obtain the titled compound (83 mg).

Yield(%): 37.6 m.p: 81–82° C.

$^1$H NMR(CDCl$_3$): δ1.22(3H,d,J=6.9 Hz), 1.25(3H,d,J= 6.9 Hz), 1.82–2.25(4H,m) 2.28(6H,s), 2.74(1H,m), 3.53(1H, m), 3.55–3.77(2H,dd, J=4.25 Hz), 4.70(2H,dd,J=17.0 Hz), 5.32(1H,s), 6.78(2H,s), 6.88(1H,s), 8.41(1H,s).

Example 14

1-[(Cyclopent-3-en-1-yl) methyl]-5-ethyl-6-(3,5-dimethylphenoxy)-2,4-pyrimidinedione.

5-Ethyl-6-(3,5-dimethylphenoxy)-2,4-pyrimidinedione and (cyclopent-3-en-1-yl)methyl toluenesulfonate were reacted by the same method with the example 1 to obtain the titled compound (68 mg).

Yield(%): 49.9 m.p: 179–180° C.

$^1$H NMR(CDCl$_3$): δ1.02(3H,t,J=7.5 Hz), 2.02–2.05(2H, m), 2.32(6H,s), 2.34(2H,m), 2.68(3H,m), 3.66(2H,d,J=7.5 Hz), 5.67(2H,s), 6.50(2H,s), 6.77(1H,s), <8.92(1H,s).

Mass: m/e 340(M$^+$), 219(100)

Example 15

1-[(Cyclopent-3-en-1-yl) methyl]-5-isopropyl-6-(3,5-dimethylphenoxy)-2,4-pyrimidinedione.

5-Isopropyll-6-(3,5-dimethylphenoxy)-2,4-pyrimidinedione and (cyclopent-3-en-1-yl)methyl toluenesulfonate were reacted by the same method with the example 1 to obtain the titled compound (73 mg).

Yield(%): 51.5 m.p: 183–184° C.

$^1$H NMR(CDCl$_3$): δ1.14(3H,s), 1.15(3H,s), 2.05(2H,dd, J=5.29 Hz), 22.31(6H,s), 2.28(2H,dd,J=8.56 Hz), 2.73–2.83 (2H,m), 3.65(2H,d,J=7.5 Hz) 5.67(2H,s), 6.50(2H,s), 6.77 (1H,s), 8.96(1H,s).

Example 16

1-[(Cyclopent-3-en-1-yl)methyl]-5-ethyl-6-(3,5-dimethylbenzoyl)-2,4-pyrimidinedione.

5-Ethyl-6-(3,5-dimethlylbenzoyl)-2,4-pyrimidinedione and (cyclopent-3-en-1-yl)methyl toluenesulfonate were reacted by the same method with the example 1 to obtain the titled compound (84 mg).

Yield(%): 59.6 m.p: 209–210° C.

$^1$H NMR(CDCl$_3$): δ0.98(3H,t,J=7.5 Hz), 2.02(2H,m), 2.26–2.37(2H,m), 2.41(6H,s), 2.68–2.73(3H,m), 3.82(2H,d, J=7.5 Hz), 5.58–5.60(2H,s), 7.34(1H,s), 8.82(1H,s).

Mass: 352(M$^+$), 219(100)

Example 17

1-[(Cyclopent-3-en-1-yl)methyl]-5-isopropyl-6-(3,5-dimethylbenzoyl)-2,4-pyrimidinedione.

pyrimidinedione and (cyclopent-3-1-yl)methyl toluenesulfonate were reacted by the same method with the example 1 to obtain the titled compound (81 mg).

Yield(%): 55.2 m.p: 196–197° C.

$^1$H NMR(CDCl$_3$): δ1.12(3H,d,J=7.0 Hz), 1.23(3H,d,J= 7.0 Hz), 2.01–2.03(2H,m), 2.26–2.34(3H,m), 2.40(6H,s), 2.58–2.62(1H,m), 3.18(1H, dd,J=7.56 Hz), 3.84(1H,dd,J= 7.56 Hz), 5.56(1H,m), 5.60 (1H,m), 7.34(1H,s), 7.51(2H,s), 8.77(1H,s).

Example 18

1-[(4-Hydroxymethylcyclopent-1-en-1-yl)methyl]-5-ethyl-6-(3,5-dimethyl-phenoxy)-2,4-pyrimidinedione 5-Ethyl-6-(3,5-dimethylphenoxy)-2,4-pyrimidinedione and (4-t-butyldimethylsilyloxymethylcyclopent-1-en-1-yl) methyl bromide were reacted by the same method with example 6 to obtain the titled compound. (52 mg)

Yield(%): 21.3

$^1$H NMR(CDCl$_3$): δ0.95(3H,t,J=7.5 Hz), 2.05(2H,m), 2.21(2H,q,J=10.0 Hz), 2.30(6H,s), 2.38–2.43(2H,m), 2.50–2.55(1H,m), 3.49(2H,d,J=5.0 Hz), 4.37(2H,s), 5.35 (1H,s), 6.52(2H,s), 6.77(1H,s), 8.99(1H,s).

Example 19

1-[(5-Hydroxymethylcyclopent-1-en-1-yl)methyl]-5-ethyl-6-(3,5-dimethyphenoxy)-2,4-pyrimidinedione 5-Ethyl-6-(3,5-dimethylphenoxy)-2,4-pyrimidinedione and (5-t-butyldimethylsilyloxymethylcyclopent-1-en-1-yl) methyl bromide were reacted by the same method with example 6 to obtain the titled compound (52 mg).

Yield(%): 21.3 m.p: 119–120° C.

$^1$H NMR(CDCl$_3$): δ0.95(3H,t,J=7.5 Hz), 1.77–1.82(1H, m), 1.98–2.04(1H,m), 2.17–2.25(2H,m), 2.30(6H,s), 3.57 (1H,d,J=5.0 Hz), 3.66(1H,d,J=5.0 Hz), 3.90(2H,d,J=14.0 Hz), 5.50(1H,s), 6.53(2H,s), 6.78(1H,s), 8.72(1H,s).

Example 20

1-[(Cyclopentyl)methyl]-5-isopropyl-6-(3,5-dimethyphenylthio)-2,4-pyrimidinedione 20-a) (Cyclopentyl)methyl toluenesulfonate To cyclopentanemethanol (2.0 g, 20 mmol) in pyridine (30 ml) was added para-toluenesulfonyl chloride (3.81 g, 20 mmol) with stirring. After 2 hrs at room temperature, the reaction mixture was concentrated for removement of pyridine, extracted with dichloromethane, dried, filtered, concentrated and separated by a column chromatography to give a desirable product (3.80 g).

Yield(%): 74.7

$^1$H NMR(CDCl$_3$): δ1.26–1.30(2H,m), 1.52–1.53(2H,m), 1.66(4H,m), 2.09(1H,m), 2.48(3H,s), 3.74(2H,d), 7.40(2H, d), 7.72(2H,d).

20-b) 1-[(Cyclopentyl)methyl]-5-isopropyl-6-(3,5-dimethylphenylthio)-2,4-pyrimidinedione.

A mixture of 5-isopropyl-6-(3,5-dimethylphenylthio)-2,4-pyrimidinedione (0.10 g, 0.40 mmol) and cyclopentyl toluenesulfonate (0.1 g, 0.4 mmol) in dimethylformamide (10 ml) were heated at 100° C. for overnight in the presence of sodium bicarbonate (41 mg, 0.48 mmol). After the concentration of dimethylformamide, the desirable product was obtained by the separation of the column chromatography to give a desirable product as a white solid (75 mg).

Yield(%): 50.3 m.p: 145–146° C.

$^1$H NMR(CDCl$_3$): δ1.20(3H,s), 1.22(3H,s), 1.26–1.30 (2H,m), 1.52–1.53(2H,m), 1.66(4H,m), 2.28(6H,s), 2.32–2.35(1H,m), 3.48–3.54(1H,m), 4.02(2H,d,J=7.5 Hz), 6.74(2H,s), 6.87(1H,s), 9.27(1H,s).

Mass: m/e 327(M$^+$), 275(100)

Example 21

1-(Cyclopentyl)methyl-5-isopropyl-6-(3,5-dimethylphenoxy)-2,4-pyrimidinedione

5-Isopropyl-6-(3,5-dimethylphenoxy)-2,4-pyrimidinedione and (cyclopentyl) methyl toluenesulfonate were reacted by the same method with example 20 to obtain the titled compound (53 mg).

Yield(%): 37.2 m.p: 157–158° C.

$^1$H NMR(CDCl$_3$): δ1.14(3H,s), 1.15(3H,s), 1.21–1.25 (2H,m), 1.53–1.55(2H,m), 1.65–1.68(4H,m), 2.26–2.29(1H, m), 2.31(6H,s), 2.78–2.83(1H,m), 3.61(2H,d,J=7.5 Hz), 6.51(2H,s), 6.77(1H,s), 9.04(1H,s).

Example 22

1-(Cyclopentyl)methyl-5-isopropyl-6-(3,5-dimethylbenzoyl)-2,4-pyrimidinedione

5-Isopropyl-6-(3,5-dimethylbenzoyl)-2,4-pyrimidinedione and (cyclopentyl)methyl toluenesulfonate were reacted by the same method with example 20 to obtain the titled compound (84 mg).

Yield(%): 57.0 m.p: 167–168° C.

$^1$H NMR(CDCl$_3$): δ1.12(3H,dJ=7.0 Hz), 1.15–1.19(2H, m), 1.23(3H,d,J=7.0 Hz), 1.46–1.47(2H,m), 1.57(4H,m), 2.10–2.16(1H,m), 2.30–2.36(1H,m), 2.41(6H,s), 3.15(1H, dd,J=7.05 Hz), 3.84(1H,dd,J=7.5 Hz), 7.34(1H,s), 7.52(2H, s), 9.02(1H,s).

Mass: m/e 368(M$^+$), 133(100)

Example 23

1-(Cyclopentyl)methyl-5-ethyl-6-(3,5-dimethylbenzoyl)-2,4-pyrimidinedione

5-Ethyl-6-(3,5-dimethylbenzoyl)-2,4-pyrimidinedione and (cyclopentyl)-methyl toluenesulfonate were reacted by the same method with example 20 to obtain the titled compound. (80 mg)

Yield(%): 56.4 m.p: 186–187° C.

$^1$H NMR(CDCl$_3$): δ0.94(3H,t,J=7.5 Hz), 1.24(3H,d,J=7.0 Hz), 1.46–1.47(2H,m), 1.56–1.58(4H,m), 2.14(1H,m), 2.41 (6H,s), 2.62(2H,q,), 3.18(1H,d,J=7.0 Hz), 3.84(1H,d,J=7.0 Hz), 7.34(1H,s), 7.51(2H,s), 8.94(1H,s).

Example 24

1-{[4-Bis(hydroxymethyl)cyclopent-1-en-1-yl] methyl}-5-ethyl-6-phenyl-thio-2,4-pyrimidinedione 24-a) [4-Bis (t-butyldimethylsilyloxylmethyl)cyclopent-1-en-1-yl]methyl bromide A mixture of carbon tetrabromide (1.99 g, 6.0 mmol) and triphenylphosphine (1.97 g, 7.5 mmol) were added to [4-bis (t-butyldimethylsilyloxymethyl)cyclopent-1-en-1-yl]methyl alcohol (1.93 g, 5.0 mmol) in dichloromethane under ice bath and then, the reaction mixture was stirred for 30 min at 0° C. After overnight at room temperature, the reaction mixture was extracted with dichloromethane, dried with $MgSO_4$, filtered, concentrated and separated by column chromatography to give a desirable product (1.43 g).

Yield(%): 63.5

$^1$H NMR(CDCl$_3$): δ0.05(6H,s), 0.90(9H,s), 2.09(2H,br), 2.15(2H, br), 3.64(4H,m), 4.04(2H,s), 5.21(1H,s).

24-b) 1-{[4-Bis(hydroxymethyl)cyclopent-1-en-1-yl] methyl}-5-ethyl-6-phenylthio-2,4-pyrimidinedione A mixture of 5-ethyl-6-phenylthio-2,4-pyrimidinedione (0.16 g, 0.66 mmol) and [4-bis(t-butyldimethylsilyloxymethyl)cyclopent-1-en-1-yl]methyl bromide (0.30 g, 0.66 mmol) in dimethylformamide (10 ml) were heated at 50° C. for overnight in the presence of sodium bicarbonate (66 mg, 0.79 mmol). After the concentration of dimethylformamide, 1-{[4-bis(t-butyldimethylsilyloxymethyl)cyclopent-1-en-1-yl)methyl}-5-ethyl-6-phenylthio-2,4-pyrimidinedione was obtained by the separation of the column chromatography. And then, this compound in THF (10 ml) was reacted with n-tetrabutylammoniumfluoride at room temperature for 1 hr. After the concentration of THF, the residue was separated by column chromatography to give a desirable product (45 mg).

Yield(%): 17.6 m.p 170–171° C.

$^1$H NMR(CDCl$_3$): δ1.02(3H,t,J=7.5 Hz), 2.09(2H,br), 2.15(2H,br), 2.68(2H, q,J=7.5 Hz), 3.64(4H,t,J=7.5 Hz), 4.62(2H,s), 5.20(1H,s), 7.16(2H,d,J=7.5 Hz), 8.40(1H,s).

Example 25

1-{[4-Bis(hydroxymethyl)cyclopent-1-en-1-yl] methyl}-5-ethyl-6-(3,5-dimethyl-phenylthio)-2,4-pyrimidinedione.

5-Ethyl-6-(3,5-dimethylphenylthio)-2,4-pyrimidinedione and [4-bis (t-butyldimethylsilyloxymethyl)cyclopent-1-en-1-yl]methyl bromide were reacted by the same method with example 24 to obtain the titled compound (48 mg).

Yield(%): 17.5 m.p: 156–157° C.

$^1$H NMR(CDCl$_3$): δ1.02(3H,t,J=7.4 Hz), 2.08(2H,s), 2.14 (2H,s), 2.28(6H,s), 2.68(2H,q,J=7.5 Hz), 3.62(4H,t,J=11.2 Hz), 4.62(2H,s), 5.21(1H,s), 6.75(1H,s), 6.88(1H,s), 9.61 (1H,s).

Mass: m/e 416(M$^+$), 91(100)

Example 26

1-{[4-Bis(hydroxymethyl)cyclopent-1-en-1-yl] methyl}-5-isopropyl-6-phenylthio-2,4-pyrimidinedione.

5-Isopropyl-6-phenylthio-2,4-pyrimidinedione and [4-bis (t-butyldimethylsilyloxymethyl)cyclopent-1-en-1-yl]methyl bromide were reacted by the same method with example 24 to obtain the titled compound (52 mg).

Yield(%): 19.6 m.p: 148–149° C.

$^1$H NMR(CDCl$_3$): δ1.19(3H,s), 1.20(3H,s), 2.06(2H,s), 2.17(2H,s), 3.45–3.51(1H,m), 3.59(4H, t,J=11.0 Hz), 4.69 (2H,s), 5.21(1H,s), 7.16(2H,d,J=7.5 Hz), 7.25(1H,t,J=7.5 Hz), 7.33(2H,t,J=7.5 Hz), 9.55(1H,s).

Example 27

1-{[4-Bis(hydroxymethyl)cyclopent-1-en-1-yl] methyl}-5-isopropyl-6-(3,5-dimethylphenylthio)2,4-pyrimidinedione.

5-Isopropyl-6-(3,5-dimethylphenylthio)-2,4-pyrimidinedione and [4-bis (t-butyldimethylsilyloxymethyl) cyclopent-1-en-1-yl]methyl bromide were reacted by the same method with example 24 to obtain the titled compound (44 mg).

Yield(%): 15.5 m.p: 156–157° C.

$^1$H NMR(CDCl$_3$): δ1.02(3H,s), 1.21(3H,s), 2.08(2H,s), 2.16(2H,s), 2.28(6H,s), 3.45–3.51(1H,m), 3.62(4H,s), 4.68 (2H,s), 5.21(1H,s), 6.76(1H,s), 6.87(1H,s), 6.69(1H,s).

Example 28

1-{[3,4-Di(hydroxymethyl)cyclopent-1-en-1-yl] methyl}-5-ethyl-6-phenylthio-2,4-pyrimidinedione 28-a) [3,4-Di(t-butyldimethylsilyloxymethyl)cyclopent-1-en-1-yl]methyl bromide A mixture of carbon tetrabromide (3.18 g, 9.6 mmol) and triphenyl phosphine (3.15 g, 12.9 mmol) were added to [3,4-di(t-butyldimethylsilyloxymethyl)cyclopent-1-en-1-yl] methyl alcohol (3.09 g, 8.0 mmol) in dichloromethane under ice bath and then, the reaction mixture was stirred for 30 min at 0° C. After overnight at room temperature, the reaction mixture was extracted with dichloromethane, dried with $MgSO_4$, filtered, concentrated and separated by column chromatography to give a desirable product (2.43 g).

Yield(%): 67.4

$^1$H NMR(CDCl$_3$): δ0.05(6H,s), 0.91(9H,s), 1.85(1H,d,J= 15.5 Hz), 2.26(2H,m), 2.62–2.70(3H,m), 3.44(1H,t,J=9.0 Hz), 3.60(2H,m), 3.78(1H,d,J=7.5 Hz), 4.08(2H,s), 5.25(1H, s).

28-b) 1-[3,4-Di(hydroxymethylcyclopent-1-en-1-yl) methyl]-5-ethyl-6-phenylthio-2,4-pyrimidinedione A mixture of 5-ethyl-6-phenylthio-2,4-pyrimidinedione (0.16 g, 0.66 mmol) and [3,4-di(t-butyldimethylsilyloxymethyl)cyclopent-1-en-1-yl]methyl bromide (0.30 g, 0.66 mmol) in dimethylformamide (10 ml) were heated at 50° C. for overnight in the presence of sodium bicarbonate (66 mg, 0.79 mmol). After the concentration of dimethylformamide, 1-{[3,4-di(t-butyldimethylsilyloxymethyl)cyclopent-1-en-1-yl]methyl}-5-ethyl-6-phenylthio-2,4-pyrimidinedione was obtained by the separation of the column chromatography. And then, this compound in THF (10 ml) was reacted with n-tetrabutylammonium fluoride at room temperature for 1 hr. After the concentration of THF, the residue was separated by column chromatography to give a desirable product (48 mg).

Yield(%): 18.7

$^1$H NMR(CDCl$_3$): δ1.03(3H,t), 1.84(1H,d,J=15.5 Hz), 2.38(2H,m), 2.60(1H,br) 2.70(2H,q,J=7.0 Hz), 3.44(1H,t,J= 9.0 Hz), 3.59–3.63(2H,m), 3.78(1H,d,J=7.5 Hz), 4.59(2H, dd, J=4.5, 7.0 Hz), 5.25(1H,s), 7.16(1H,d, J=7.5 Hz), 7.26 (1H,t, J=8.5 Hz), 7.34(2H,t, J=7.5 Hz), 9.30(1H,s).

Example 29

1-{[3,4-Di(hydroxymethyl)cyclopent-1-en-1-yl] methyl}-5-ethyl-6-(3,5-di-methylphenylthio)-2,4-pyrimidinedione 5-Ethyl-6-(3,5-dimethylphenylthio)-2,4-pyrimidinedione and [3,4-di(t-butyldimethylsilyloxymethyl)cyclopent-1-en- 1-yl]methyl bromide were reacted by the same method with example 28 to obtain the titled compound (53 mg).

Yield(%): 19.3 m.p: 156–157° C.

$^1$H NMR(CDCl$_3$): δ1.03(3H,t,J=7.5 Hz), 1.86(1H,d,J=15.5 Hz), 2.28(6H,s), 2.42(2H,m), 2.60(1H,m), 2.68–2.73 (2H,m), 3.44(1H,t,J=7.5 Hz), 3.56–3.64(2H,m), 3.79(1H,d, J=7.5 Hz), 4.59(2H,d,J=8.5 Hz), 5.27(1H,s), 6.76(2H,s), 6.88(1H,s), 9.44(1H,s).

Example 30

1-{[3,4-Di(hydroxymethyl)cyclopent-1-en-1-yl] methyl}-5-isopropyl-6-(3,5-dimethylphenylthio)-2,4-pyrimidinedione 5-Isopropyl-6-(3,5-dimethylphenylthio)-2,4-pyrimidinedione and [3,4-di(t-butyldimethylsilyloxymethyl)cyclopent-1-en-1-yl]methyl bromide were reacted by the same method with example 28 to obtain the titled compound (51 mg).

Yield(%): 17.9 m.p: 136–137° C.

$^1$H NMR(CDCl$_3$): δ1.20(3H,d,J=7.0 Hz), 1.25(3H,d,J=7.0 Hz), 1.87(1H,d,J=15.5 Hz), 2.28(6H,s), 2.40–2.44(2H, m), 2.60(1H,br), 2.96–3.00(1H,m), 3.44–3.53(2H,m), 3.58–3.65(1H,m), 3.80(1H, dd,J=4.0, 6.5 Hz), 4.62–4.69 (2H,m), 5.27(1H,s), 6.76(2H,s), 6.88(1H,s), 9.01(1H,s).

Example 31

1-{[3,4-Di(hydroxymethyl)cyclopent-1-en-1-yl] methyl}-5-ethyl-6-(3,5-dimethylphenoxy)-2,4-pyrimidinedione 5-Ethyl-6-(3,5-dimethylphenoxy)-2,4-pyrimidinedione and [3,4-di(t-butyldimethylsilyloxymethyl)cyclopent-1-en-1-yl]methyl bromide were reacted by the same method with example 28 to obtain the titled compound (42 mg).

Yield(%): 17.9

$^1$H NMR(CDCl$_3$): δ0.94(3H,t), 1.82(1H,d,J=15.5 Hz), 2.18–2.22(2H,m), 2.31(6H,s), 2.38–2.45(2H,m), 2.76(1H, br), 3.42–3.49(2H,m), 3.60(1H,m), 3.94(1H,m), 4.33(2H, dd,J=15.5, 29.5 Hz), 5.43(1H,s), 6.52(2H,s), 6.78(1H,s), 9.79(1H,s).

Example 32

1-{[3,4-Di(hydroxymethyl)cyclopent-1-en-1-yl] methyl}-5-isopropyl-6-(3,5-dimethylphenoxy)-2,4-pyrimidinedione 5-Isopropyl-6-(3,5-dimethylphenoxy)-2,4-pyrimidinedione and [3,4-di(t-butyldimethylsilyloxymethyl)cyclopent-1-en-1-yl]methyl bromide were reacted by the same method with example 28 to obtain the titled compound (48 mg).

Yield(%): 17.5

$^1$H NMR(CDCl$_3$): δ1.21(3H,d,J=7.0 Hz), 1.24(3H,d,J=7.0 Hz), 1.83(1H,d,J=15.5 Hz), 2.31(6H,s), 2.37(2h,m), 2.57 (1H,br), 2.74–2.79(1H,m), 3.38–3.50(2H,m), 3.60(1H,q,J=5.0 Hz), 3.90(1H,d,J=7.0 Hz), 4.25(1H, d,J=16.0 Hz), 4.34 (1H,d,J=16.0 Hz), 5.42(1H,s), 6.51(2H,s), 6.77(1H,s), 9.33 (1H,s).

Example 33

1-{[3,4-Di(hydroxymethyl)cyclopent-1-en-1-yl] methyl}-5-ethyl-6-(3,5-dimethylbenzoyl)-2,4-pyrimidinedione 5-Ethyl-6-(3,5-dimethylbenzoyl)-2,4-pyrimidinedione and [3,4-di(t-butyldimethylsilyloxymethyl)cyclopent-1-en-1-yl]methyl bromide were reacted by the same method with example 28 to obtain the titled compound (68 mg).

Yield(%): 25.0 m.p: 79–80° C.

$^1$H NMR(CDCl$_3$): δ0.94–0.97(3H,t,J=7.5 Hz). 1.54(1H, d,J=15.5 Hz), 2.03–2.04(1H,m), 2.31–2.35(5H,m), 2.39(3H, s), 2.40(3H,s), 3.27–3.33(1H,m), 3.41(1H,m), 3.50(1H,m), 3.79(1H,m), 4.31(1H,m), 4.40(1H,d), 5.34(1H,m), 7.31(1H, s), 7.49(2H,s), 9.06(1H,s).

Example 34

1-{[3,4-Di(hydroxymethyl)cyclopent-1-en-1-yl] methyl}-5-isopropyl-6-(3,5-dimethylbenzoyl)-2,4-pyrimidinedione 5-Isopropyl-6-(3,5-dimethylbenzoyl)-2,4-pyrimidinedione and [3,4-di(t-butyldimethylsilyloxymethyl)cyclopent-1-en-1-yl]methyl bromide were reacted by the same method with example 28 to obtain the titled compound (74 mg).

Yield(%): 26.3 m.p: 81–82° C.

$^1$H NMR(CDCl$_3$): δ1.20(3H,d,J=7.0 Hz), 1.24(3H,d,J=7.0 Hz), 1.50(1H,d,J=15.5 Hz), 2.24–2.31(2H,m), 2.39(3h, s), 2.40(3H,s), 2.54(2H,m), 3.29(1H,m), 3.40(1H, br), 3.49 (1H,m), 3.71–3.84(1H,m), 4.27–4.39(1H,m), 5.20–5.34(1H, m), 7.33(1H,s), 7.49(2H,s), 9.39(1H,s).

Example 35

1-[2-(Cyclopent-1-en-1-yl)ethyl]-5-ethyl-6-(3,5-dimethylbenzoyl)-2,4-pyrimidinedione 35-a) 2-(Cyclopent-1-en-yl)ethyl toluenesulfonate A para-toluenesulfonylchloride (3.81 g, 20 mmol) was added to the pyridine (30 ml) solution of 2-(cyclopent-1-en-1-yl)ethyl alcohol (2.24 g, 20 mmol) and then the reaction mixture was stirred at room temperature for 2 hrs. After the removal of pyridine, the residue was extracted with dichloromethane, washed with 1N HCl, dried, filtered and separated by column chromatography to give a desirable product (2.80 g).

Yield(%): 52.6

$^1$H NMR(CDCl$_3$): δ0.82(2H,m), 1.99–2.30(6H,m), 2.49 (3H,s), 3.51(1H,m), 4.03(1H,m), 5.22(1H,s), 7.41(2H,d), 7.74(2H,d).

35-b) 1-[2-(Cyclopent-1-en-1-yl)ethyl]-5-ethyl-6-(3,5-dimethylbenzoyl)-2,4-pyrimidinedione A mixture of sodium bicarbonate (0.10 g, 1.2 mmol) and lithium iodide (13 mg, 0.1 mmol) were added to dimethylformamide solution (10 ml) of 5-ethyl-6-(3,5-dimethylbenzoyl)-2,4-pyrimidinedione (0.27 g, 1.0 mmol) and 2-(cyclopent-1-en-1-yl)ethyl toluenesulfonate (0.27 g, 1.0 mmol). And then, the reaction mixture was stirred at 90° C. for overnight, concentrated for removement of dimethylformamide, extracted with dichloromethane, dried, filtered and separated by column chromatography to give a desirable product as a white solid (148 mg).

Yield(%): 40.4 m.p: 211–213° C.

$^1$H NMR(CDCl$_3$): δ0.81(2H,dd,J=7.0,1.5 Hz), 0.97(3H,t, J=7.5 Hz), 1.99–2.30(6H,m), 2.40(6H,s), 3.29(1H,m), 3.91 (1H,m), 5.22(1H,s), 7.35(1H,s), 7.50(2H,s), 8.81(1H,s).

Mass: m/e 366(M$^+$), 94(100)

Example 36

1-[2-(Cyclopent-3-en-1-yl)ethyl]-5-ethyl-6-(3,5-dimethylbenzoyl)-2,4-pyrimidinedione 36-a) 2-(Cyclopent-3-en-1-yl)ethyl toluenesulfonate A para-toluenesulfonylchloride (3.81 g, 20 mmol) was added to the pyridine (30 ml) solution of 2-(cyclopent-3-en-1-yl)ethyl alcohol (2.24 g, 20 mmol) and then the reaction mixture was stirred at room temperature for 2 hrs. After the removal of pyridine, the residue was extracted with dichloromethane, washed with 1N HCl, dried, filtered and separated by column chromatography to give a desirable product (3.24 g).

Yield(%): 60.8

$^1$H NMR(CDCl$_3$): δ1.69(2H,m), 1.85(2H,m), 2.02(2H, m), 2.25(1H,m), 3.42(1H,m), 3.94(1H,m), 5.56(2H,d), 7.4192H,d), 7.74(2H,d).

36-b) 1-[2-(Cyclopent-3-en-1-yl)ethyl]-5-ethyl-6-(3,5-dimethylbenzoyl)-2,4-pyrimidine A mixture of sodium bicarbonate (0.10 g, 1.2 mmol) and lithium iodide (13 mg, 0.1 mmol) were added to dimethylformamide solution (10 ml) of 5-ethyl-6-(3,5-dimethylbenzoyl)-2,4-pyrimidinedione (0.27 g, 1.0 mmol) and 2-(cyclopent-3-en-1-yl)ethyl toluenesulfonate (0.27 g, 1.0 mmol). And then, the reaction mixture was stirred at 90° C. for overnight, concentrated for removal of dimethylformamide, extracted with dichloromethane, dried, filtered and separated by column chromatography to give a desirable product as a white solid (136 mg).

Yield(%): 37.1 m.p: 190–191° C.

$^1$H NMR(CDCl$_3$): δ0.97(3H,t,J=7.5 Hz), 1.69(2H,m), 1.85(2H,m), 2.02(2H,m), 2.25(1H,m), 2.37(3H,m), 2.41 (6H,s), 3.17(1H,m), 3.82(1H, m), 5.56(2H,d), 7.36(1H,s), 7.53(2H,s), 8.64(1H,s).

Mass: m/e 366(M$^+$), 94(100)

Example 37

1-[2-(Cyclopent-3-en-1-yl)ethyl]-5-isopropyl-6-(3,5-dimethylbenzoyl)-2,4-pyrimidinedione 5-Isopropyl-6-(3,5-dimethylbenzoyl)-2,4-pyrimidinedione and 2-(cyclopent-3-en-1-yl)ethyl toluenesulfonate were reacted by the same method with example 35 to obtain the titled compound (140 mg).

Yield(%): 36.8 m.p: 175–176° C.

$^1$H NMR(CDCl$_3$): δ1.13(3H,d,J=7.0 Hz), 1.20(3H,d,J= 7.0 Hz), 1.70(2H,m), 1.82(2H,m), 2.03(1H,m), 2.33(3H,m), 2.41(6H,s), 3.13(1H,m), 3.80(1H,m), 5.56(2H,dd,J=4.0,10.0 Hz), 7.36(1H,s), 7.55(2H,s), 8.45(1H,s).

Example 38

1-[2-(Cyclopent-3-en-1-yl)ethyl]-5-isopropyl1–6-(3,5-dimethylphenoxy)-2,4-pyrimidinedione 5-Isopropyl-6-(3,5-dimethyl2phenoxy)-2,4-pyrimidinedione and 2-(cyclopent-3-en-1-yl)ethyl toluenesulfonate were reacted by the same method with example 35 to obtain the titled compound (109 mg).

Yield(%): 29.6 m.p: 109–110° C.

$^1$H NMR(CDCl$_3$,): δ1.14(6H,d,J=7.0 Hz), 1.70(2H,m), 1.93(2H,m), 2.15(1H,m), 2.31(6H,s), 2.45(2H,m), 2.79(1H, m), 3.67(2H,t,J=7.5 Hz), 5.62(2H,s), 6.53(2H,s), 6.78(1H,s), 8.83(1H,s).

Example 39

1-[2-(Cyclopent-3-en-1-yl)ethyl]-5-isopropyl-6-(3,5-dimethylphenylthio)-2,4-pyrimidinedione 5-Isopropyl-6-(3,5-dimethylphenylthio)-2,4-pyrimidinedione and 2-(cyclopent 3-en-1-yl)ethyl toluenesulfonate were reacted by the same method with example 35 to obtain the titled compound (134 mg).

Yield(%): 34.8 m.p: 128–129° C.

$^1$H NMR(CDCl$_3$): δ1.24(6H,d,J=7.0 Hz), 1.68(2H,m), 2.03(2H,m), 2.18(1H,m), 2.29(6H,s), 2.48(2H,m), 3.53(1H, m), 400(2H,t,J=8.0 Hz), 5.64(2H,s), 6.77(2H,s), 6,88(1H,s), 8.95(1H,s).

Mass: m/e 384(M$^+$), 247(100)

Example 40

1-{2-(Cyclopent-2-en-1-yl)ethyl]-5-ethyl-6-(3,5-dimethylbenzoyl)-2,4-pyrimidinedione 40-a) 2-(Cyclopent-2-en-1-yl)ethyl bromide A mixture of carbon tetrabromide (19.2 g, 57.8 mmol) and triphenyl phosphine (15.2 g, 57.8 mmol) were added to 2-(cyclopent-2-en-1-yl)ethyl alcohol (4.32 g, 38.5 mmol) in dichloromethane (15 ml) under ice bath and then, the reaction mixture was stirred for 2 hrs at 0° C. The reaction mixture was extracted with dichloromethane, dried with MgSO$_4$, filtered, concentrated and separated by column chromatography to give a desirable product (5.53 g).

Yield(%): 82.0

$^1$H NMR(CDCl$_3$): δ1.26–2.29(6H,m), 2.80(1H,m), 3.43 (2H,t), 5.72(2H,s).

40-b) 1-[2-(Cyclopent-2-en-1-yl)ethyl]-5-ethyl-6-(3,5-dimethylbenzoyl)-2,4-pyrimidinedione A mixture of sodium bicarbonate (0.10 g, 1.2 mmol) and lithium iodide (13 mg, 0.1 mmol) were added to dimethylformamide solution (10 ml) of 5-ethyl-6-(3,5-dimethylbenzoyl)-2,4-pyrimidinedione (0.27 g, 1.0 mmol) and 2-(cyclopent-2-en-yl))ethyl bromide (0.18 g, 1.0 mmol). And then, the reaction mixture was stirred at 90° C. for overnight, concentrated for removement of dimethylformamide, extracted with dichloromethane, dried, filtered and separated by column chromatography to give a desirable product as a white solid (112 mg).

Yield(%): 30.6 m.p: 183–185° C.

$^1$H NMR(CDCl$_3$): δ0.97(3H,t), 1.24(1H,m), 1.49(1H,m), 1.70(2H,m), 2.00(1H,m), 2,24(2H,m), 2.41(6H,s), 2.49(1H, m), 3.23(1H,m), 3.81(1H,m), 5.48(1H,m), 5.66(1H,m), 7.35 (1H,s), 7.52(2H,s), 8.73(1H,s).

Example 41

1-[2-(Cyclopent-2-en-1-yl)ethyl]-5-isopropyl-6-(3,5-dimethylbenzoyl)-2,4-pyrimidinedione 5-Isopropyl-6-(3,5-dimethylbenzoyl)-2,4-pyrimidinedione and 2-(cyclopent-2-en-1-yl)ethyl bromide were reacted by the same method with example 40 to obtain the titled compound (123 mg).

Yield(%): 32.3

$^1$H NMR(CDCl$_3$): δ1.15(3H,d,J=6.85 Hz), 1.23(3H,d,J= 6.85), 1.29(1H,m), 1.42(1H,m), 1.75(2H,m), 1.92(1H,m), 2.05(1H,m), 2.29(2H,m), 2.45(6H,s), 2.52(1H,m), 3.35(1H, m), 3.92(1H,m), 5.50(1H,m), 5.73(1H,m), 7.92(1H,s), 7.48 (2H,s), 8.85(1H,s).

Example 42

1-[2-(Cyclopent-2-en-1-yl)ethyl]-5-isopropyl-6-(3,5-dimethylphenoxy)-2,4-pyrimidinedione 5-Isopropyl-6-(3,5-dimethylphenoxy)-2,4-pyrimidinedione and 2-(cyclopent-2-en-1-yl)ethyl bromide were reacted by the same method with example 40 to obtain the titled compound (132 mg).

Yield(%): 35.8 m.p: 148–149° C.

$^1$H NMR(CDCl$_3$): δ1.15(6H,d), 1.36(1H,m), 1.55(1H,m), 1.70(1H,m), 2.00(1H,m), 2.27(2H,m), 3.69(2H,m), 5.56 (1H,dd,J=2.05 Hz), 5.71(1H,dd,J=2.25 Hz), 6.54(2H,s), 6.78(1H,s), 8.37(1H,s).

Example 43

1-[2-(Cyclopent-2-en-1-yl)ethyl]-5-isopropyl-6-(3,5-dimethylphenylthio)-2,4-pyrimidinedione 5-Isopropyl-6-(3,5-dimethylphenylthio)-2,4-pyrimidinedione and 2-(cyclopent-2-en-1-yl)ethyl bromide were reacted by the same method with example 40 to obtain the titled compound (98 mg).

Yield(%): 25.5 m.p: 138–140° C.

$^1$H NMR(CDCl$_3$): δ1.25(6H,dd,J=1.85 Hz), 1.45(1H,m), 1.57(1H,m), 1.68(2H,m), 2.01(1H,m), 2.29(6H,s), 2.35(1H,m), 2.61(1H,m), 3.53(1H,m), 4.02(2H,t), 5.59(1H,dd,J=2.0 Hz), 5.72(1H,dd,J=2.25 Hz), 6.77(2H,s), 6.88(1H,s), 8.67 (1H,s).

Example 44

1-(2-Cyclopentyl)ethyl-5-ethyl-6-(3,5-dimethylbenzoyl)-2,4-pyrimidinedione 44-a) (2-Cyclopentyl)ethyl toluenesulfonate A para-toluenesulfonyl chloride (16.0 g, 83.8 mmol) was added to the pyridine (250 ml) solution of (2-cyclopentyl) ethyl alcohol (8.76 g, 76.2 mmol) and then the reaction mixture was stirred at room temperature for 6 hrs. After the removal of pyridine, the residue was extracted with ethyl acetate, washed with 1N HCl, dried, filtered and separated by column chromatography to give a desirable product (15.7 g).

Yield(%): 73

$^1$H NMR(CDCl$_3$): δ0.90–1.89(11H,m), 2.45(3H,s), 4.05 (2H,t), 7.27–7.88(4H,dd).

44-b) 1-(2-Cyclopentyl)ethyl-5-ethyl-6-(3,5-dimethylbenzoyl)-2,4-pyrimidinedione A mixture of sodium bicarbonate (0.10 g, 1.2 mmol) and lithium iodide (13 mg, 0.1 mmol) were added to dimethylformamide solution (10 ml) of 5-ethyl-6-(3,5-dimethylbenzoyl)-2,4-pyrimidinedione (0.27 g, 1.0 mmol) and 2-(cyclopentyl)ethyl toluenesulfonate (0.27 g, 1.0 mmol). And then, the reaction mixture was stirred at 90° C. for overnight, concentrated for removement of dimethylformamide, extracted with dichloromethane, dried, filtered and separated by column chromatography to give a white solid (90 mg).

Yield(%): 24.5

$^1$H NMR(CDCl$_3$): δ0.95(2H,m), 0.97(3H,t), 1.41–1.62 (9H,m), 2.02(1H,m), 2.28(1H,m), 2.41(6H,s), 3.18(1H,m), 3.79(1H,m), 7.35(1H,s), 7.52(2H,s), 8.64(1H,s).

Example 45

1-(2-Cyclopentyl)ethyl-5-isopropyl-6-(3,5-dimethylbenzoyl)-2,4-pyrimidinedione

5-Isopropyl-6-(3,5-dimethlylbenzoyl)-2,4-pyrimidinedione and (2-cyclopentyl)ethyl toluenesulfonate were reacted by the same method with example 44 to obtain the titled compound (95 mg).

Yield(%): 24.9 m.p: 174–176° C.

$^1$H NMR(CDCl$_3$): δ0.95(2H,m), 1.15(3H,d,J=6.85 Hz), 1.23(3H,d,J=6.85 Hz), 1.391.69(9H,m), 2.32(1H,m), 2.41 (6H,s), 3.15(1H,m), 3.77(1H,m) 7.36(1H,s), 7.55(2H,s), 8.90(1H,s).

Example 46

1-(2-Cyclopentyl)ethyl-5-isopropyl-6-(3,5-dimethylphenoxy)-2,4-pyrimidinedione

5-Isopropyl-6-(3,5-dimethylphenoxy)-2,4-pyrimidinedione and (2-cyclopentyl)ethyl toluenesulfonate were reacted by the same method with example 44 to obtain the titled compound (105 mg).

Yield(%): 28.3 m.p: 136–138° C.

$^1$H NMR(CDCl$_3$): δ1.04(2H,m), 1.15(6H,d), 1.46–1.71 (9H,m), 2.31(6H,s) 2.80(1H,m), 3.65(2H,t), 6.53(2H,s), 6.78(1H,s), 8.60(1H,s).

Example 47

1-(2-Cyclopentyl)ethyl-5-isopropyl-6-(3,5-dimethylphenylthio)-2,4-pyrimidinedione 5-Isopropyl-6-(3,5-dimethylphenoxy)-2,4-pyrimidinedione and (2-cyclopentyl)ethyl toluenesulfonate were reacted by the same method with example 44 to obtain the titled compound (80 mg).

Yield(%): 20.7 m.p: 95–97° C.

$^1$H NMR(CDCl$_3$): δ1.11(2H,m), 1.25(6H,d), 1.47–1.78 (9H,m), 2.29(6H, s), 3.53(1H,m), 4.00(2H,t), 6.77(2H,s), 6.88(1H,s), 9.1991H,s).

Example 48

1-[2-Bis(hydroxymethyl)cyclopropane-1-yl]methyl-5-ethyl-6-phenylthio-2,4-pyrimidinedione A sodium bicarbonate (0.10 g, 1.2 mmol) was added to a stirred solution of dimethylformamide (10 ml) of 5-ethyl-6-phenylthio-2,4-pyrimidinedione (0.25 g, 1.0 mmol) and 2-bis(t-butyldimethylsilyloxymethyl)cyclopropane-1-yl] methyl bromide (0.42 g, 1.0 mmol) and then, the reaction mixture was heated at 90° C. for overnight. The reaction mixture was poured into water (30 ml), extracted with ether (2 times), dried, filtered, concentrated and separated by column chromatography to give 1-[2-bis(t-butyldimethylsilyloxymethyl)cyclopropane-1-yl]methyl-5-ethyl -6-phenylthio-2,4-pyrimidinedione as a pale yellow oil (125 mg). This compound in THF (5 ml) was reacted with n-tetrabutylammonium fluoride (1.0 ml of 1.0 mol THF solvent) at room temperature for 6 hrs.

The reaction mixture was concentrated for removement of THF and separated by column chromatography to give 1-[2-bis(hydroxymethyl)cyclopropane-1-yl]methyl-5-ethyl-6-phenylthio-2,4-pyrimidinedione (142 mg) as a white solid.

Yield(%): 39.4 m.p: 118–119° C.

$^1$H NMR(CDCl$_3$): δ0.22(1H,t,J=5.5 Hz), 0.53(1H,dd,J= 5.5, 3.5 Hz), 1.05(3H,t,J=7.0 Hz), 1.07(1H,m), 2.70–2.75 (1H,m), 3.25(1H,d,J=11.0 Hz), 3.53(1H,d,J=13.0 Hz), 3.75

(1H,d,J=11.5 Hz), 4.05–4.13(2H,m), 4.20(1H,dd,J=4.0, 11.0 Hz), 7.20(2H,d), 7.28(1H,t), 7.36(2H,t), 9.36 1H,s).

Example 49

1-[2-Bis(hydroxymethyl)cyclopropane-1-yl]methyl-5-ethyl-(3,5-dimethylphenylthio)-2,4-pyrimidinedione 5-Ethyl-6-(3,5-dimethylphenylthio)-2,4-pyrimidinedione and 2-bis(t-butyldimethylsilyloxymethyl)cyclopropane-1-yl]methyl bromide were reacted by the same method with example 48 to obtain the titled compound (191 mg).

Yield(%): 49.0 m.p: 111–112° C.

$^1$H NMR(CDCl$_3$): δ0.22(1H,t,J=5.0 Hz), 0.53(1H,dd,J=8.5, 5.5 Hz), 1.04(3H,t,J=7.5 Hz), 1.37–1.42(1H,m), 2.29 (6H,s), 2.71–2.74(2H,m), 3.28(1H,d,J=10.0 Hz), 3.53(1H, dJ=12.5 Hz), 3.73(1H,d,J=11.0 Hz), 4.05–4.14(2H,m), 4.19 (1H,d,J=11.5 Hz), 6.79(2H,s), 6.89(1H,s), 9.45(1H,s).

Example 50

1-[2-Bis(hydroxymethyl)cyclopropane-1-yl]methyl-5-ethyl-6-(3,5-dimethylphenoxy)-2,4-pyrimidinedione 5-Ethyl-6-(3,5-dimethylphenoxy)-2,4-pyrimidinedione and 2-bis(t-butyldimethylsilyloxymethyl)cyclopropane-1-yl]methyl bromide were reacted by the same method with example 48 to obtain the titled compound (151 mg).

Yield(%): 40.3

$^1$H NMR(CDCl$_3$): δ0.27(1H,t,J=5.5 Hz), 0.59(1H,dd,J=5.0, 3.5 Hz), 0.94(3H,t,J=7.5 Hz), 1.26(1H,m), 2.17–2.24 (2H,m), 2.32(6H,s), 3.29 1H,d,J=11.0 Hz), 3.55(1H,d,J=12.5 Hz), 3.80(2H,d,J=11.0 Hz), 3.98(1H,dd,J=8.5, 6.0 Hz), 4.12(1H,d,J=12.5 Hz) 6.79(2H,s), 6.80(1H,s), 9.01(1H,s).

Example 51

1-[2-Bis(hydroxymethyl)cyclopropane-1-yl]methyl-5-ethyl-6-(3,5-dimethylbenzoyl)-2,4-pyrimidinedione 5-Ethyl-6-(3,5-dimethylbenzoyl)-2,4-pyrimidinedione and 2-bis(t-butyldimethylsilyloxymethyl)cyclopropane-1-yl]methyl bromide were reacted by the same method with example 48 to obtain the titled compound (202 mg).

Yield(%): 52.4 m.p: 79.5–80.4° C.

$^1$H NMR(CDCl$_3$): δ0.10(1H,t,J=5.5 Hz), 0.61(1H,dd,J=9.0, 5.5 Hz), 0.98(3H,t,J=7.0 Hz), 1.21(1H,m), 2.26(2H,m), 2.41(6H,s), 3.35(1H,d,J=11.0 Hz), 3.45(1H,d,J=12.0 Hz), 3.70–3.81(2H,m), 4.01–4.13(2H,m), 7.36(1H,s), 7.52(1H,s), 7.59(1H,s), 8.97(1H,s).

Example 52

1-[2-Bis(hydroxymethyl)cyclopropane-1-yl]methyl-5-isopropyl-6-phenylthio-2,4-pyrimidinedione 5-Isopropyl-6-phenylthio-2,4-pyrimidinedione and 2-bis(t-butyldimethyl silyloxymethyl)cyclopropane-1-yl]methyl bromide were reacted by the same method with example 48 to obtain the titled compound (106 mg).

Yield(%): 42.5

$^1$H NMR(CDCl$_3$): δ0.24(1H,t,J=5.5 Hz), 0.55(1H,dd,J=8.0, 5.5 Hz), 1.12(1H,m), 1.20(3H,t,J=7.0 Hz), 1.26(3H,t,J=7.0 Hz), 2.75–2.81(1H,m), 3.21(1H,d,J=11.0 Hz), 3.56(1H, d,J=12.0 Hz), 3.84(1H,d,J=11.0 Hz), 4.11–4.14(2H,m), 4.25 (1H,dd,J=4.0, 11.0 Hz), 7.21(2H, d), 7.29(1H,t), 7.36(2H,t), 8.26(1H,s).

Example 53

1-[2-Bis(hydroxymethyl)cyclopropane-1-yl]methyl-5-isopropyl-6-(3,5-dimethylphenylthio)-2,4-pyrimidinedione 5-Isopropyl-6-(3,5-dimethylphenylthio)-2,4-pyrimidinedione and 2-bis(t-butyl dimethylsilyloxymethyl)cyclopropane-1-yl]methyl bromide were reacted by the same method with example 48 to obtain the titled compound (211 mg).

Yield(%): 52.1 m.p: 111.3–112.6° C.

$^1$H NMR(CDCl$_3$): δ0.24(1H,t,J=5.5 Hz), 0.55(1H,dd,J=8.0, 5.5 Hz), 1.10(1H,m), 1.21(3H,d,J=7.0 Hz), 1.26(3H,d, J=7.0 Hz), 2.75–2.81(1H,m), 0.26(1H,d,J=11.0 Hz), 3.56 (1H,d,J=12.0 Hz), 3.75(1H,d,J=11.0 Hz), 4.11–4.13(2H,m), 4.25(1H,dd,J=4.0, 11.0 Hz), 6.75(2H,s), 6.89(1H,s), 9.00 (1H,s).

Example 54

1-[2-Bis(hydroxymethyl)cyclopropane-1-yl]methyl-5-isopropyl-6-(3,5-dimethylphenoxy)-2,4-pyrimidinedione 5-Isopropyl-6-(3,5-dimethylphenoxy)-2,4-pyrimidinedione and [2-bis(t-butyldimethylsilyloxymethyl)cyclopropane-1-yl]methyl bromide were reacted by the same method with example 48 to obtain the titled compound (168 mg).

Yield(%): 43.2 m.p: 90.8–91.6° C.

$^1$H NMR(CDCl$_3$): δ0.24(1H,t,J=5.5 Hz), 0.58(1H,dd,J=5.0, 3.5 Hz), 1.12(3H,d,J=7.0 Hz), 1.15(3H,d,J=7.0 Hz), 1.20–1.22(1H,m), 2.32(6H,s), 2.75–2.81(1H,m), 3.28(1H,d, J=11.0 Hz), 3.54(1H,d,J=12.0 Hz), 3.75–3.79(2H,m), 3.94 (1H,dd,J=8.5, 6.0 Hz), 4.10(1H,d,J=12.0 Hz), 6.57(2H,s), 6.79(1H,s), 8.70(1H,s).

Example 55

1-[2-Bis(hydroxymethyl)cyclopropane-1-yl]methyl-5-isopropyl-6-(3,5-dimethylbenzoyl)-2,4-pyrimidinedione 5-Isopropyl-6-(3,5-dimethylbenzoyl)-2,4-pyrimidinedione and [2-bis(t-butyldimethylsilyloxymethyl)cyclopropane-1-yl]methyl bromide were reacted by the same method with example 48 to obtain the titled compound (194 mg).

Yield(%): 48.5 m.p: 91–92° C.

$^1$H NMR(CDCl$_3$): δ0.07(1H,t,J=5.5 Hz), 0.60(1H,dd,J=9.0, 5.0 Hz), 1.13(3H,t,J=6.5 Hz), 1.23(3H,d,J=8.0 Hz), 1.25(1H,m), 2.33–2.35(1H,m), 2.41(6H,s), 3.28(1H,d,J=12.0 Hz), 3.35(1H,d,J=12.5 Hz), 3.68–3.77(2H,m), 3.96–4.12(2H,m), 7.36(1H,s), 7.54(1H,s), 7.60(1H,s), 8.84 (1H,s).

Experimental Example

Antiviral activity and Toxicity test

The anti-HIV assays were based on the inhibition of the virus-induced cytopathic effect in MT-4 cells as a described method in J. Med. Chem, 34, 357, 1991. Briefly, MT-4 cells were suspended in culture medium at $2.5 \times 10^5$ cells/ml and infected with 1000 $CCID_{50}$ (50% cell culture infective dose) of HIV. Immediately, after virus infection, 100 μl of the cell suspension was brought into each well of a flat-bottomed microtitray containing various concentrations of the test compounds. After a 4 or 5 days incubation at 37° C., the number of viable cells was determined by the 3-(4,5-dimethylthiazol-2-yl)-2,5-diphenyltetrazolium bromide (MTT) method, as disclosed in J. Virol. Methods, 20, 309, 1988. The cytotoxicity of the compounds of the present invention was assessed in parallel with their antiviral activity. It was based on the viability of mock-infected host cells as determined by the MTT methods.

The results of the tests are shown in table.

| Examples | $CD_{50}$ | $ED_{50}$ | S.I. |
|---|---|---|---|
| 2 | 7.86 | 0.000129 | 60,930 |
| 4[a] | 11.40 | 0.0054 | 2,111 |
| 7 | 7.69 | 0.00256 | 3,004 |
| 9 | 8.51 | 0.000507 | 16,785 |
| 14[b] | 16.81 | 0.000042 | 400,238 |
| 15[a] | 10.07 | 0.0062 | 1,624 |
| 16[c] | 1.52 | 0.0000000106 | 143,396,226 |
| 17[a] | 19.16 | 0.0053 | 3,615 |
| 18 | 12.78 | 0.0113 | 1,131 |
| 19 | 55.37 | 0.040 | 1,384 |
| 20[b] | 11.38 | 0.000469 | 24,264 |
| 21[b] | 10.04 | 0.00326 | 3,089 |
| 22[b] | 9.97 | 0.0000000142 | 702,112,676 |
| 23[d] | >100 | <0.00026 | >384,615 |
| 25 | 14.64 | 0.0053 | 2,762 |
| 35[d] | 28.58 | 0.00287 | 9,958 |
| 36[d] | 10.30 | 0.00034 | 30,294 |
| 37[d] | 9.23 | 0.00069 | 13,377 |
| 40[e] | 7.11 | <0.00026 | >27,346 |
| 42[e] | 7.53 | 0.0032 | 2,353 |
| 44[e] | 8.58 | 0.00144 | 5,958 |
| 48[c] | 96.95 | 0.105 | 923 |
| 49[c] | 21.56 | 0.00118 | 18,271 |
| 50[c] | 111.79 | 0.0144 | 7,763 |
| 51[c] | 128.95 | 0.0106 | 12,165 |
| 52[c] | 104.12 | 0.0696 | 1,496 |
| 53[c] | 13.39 | 0.00186 | 7,199 |
| 54[c] | 7.69 | 0.00256 | 3,004 |
| 55[c] | 131.71 | 0.00604 | 21,806 |
| AZT | 1.58 | 0.0006 | 2,633 |
| AZT[a] | 1.13 | 0.000194 | 5,825 |
| AZT[b] | 0.73 | 0.00065 | 1,123 |
| AZT[c] | 0.057 | 0.000688 | 83 |
| AZT[d] | 2.75 | 0.0005 | 5,500 |
| AZT[e] | 1.84 | 0.00058 | 3,172 |

It was found that the compounds of present invention have the superior antiviral activities to this control, AZT.

Example of pharmaceutical preparations

Injectable preparations were prepared with the ingredients of the following tables by the conventional injection manufacturing method.

| | ingredients | the amount used |
|---|---|---|
| ampul (5 ml) | compound of example 4 | 10 mg |
| | polyoxy40hydrogenated caster oil | 2 mg |
| | lidocaine.HCl | 5 mg |
| | anhydrous citric acid | 0.3 mg |
| | sodium citrate | 0.1 mg |
| | sodium chloride | q.s |
| | ethanol | 1 ml |
| | distillation water for injection | q.s |

Vials were prepared with the ingredients of the following tables by the conventional manufacturing method.

| | | |
|---|---|---|
| Vials (150 mg) | compound of example 4 | 100 mg |
| | methylparaben | 1.0 mg |
| | propylparaben | 0.5 mg |
| | anhydrous citric acid | 30 mg |
| | sodium citrate | 18.5 mg |

Tablets were prepared with the ingredients of the following tables by the conventional manufacturing method.

| | | |
|---|---|---|
| tablet (700 mg) | compound of example 4 | 250 mg |
| | corn starch | 130 mg |
| | microcrystalline cellulose | 50 mg |
| | lactose monohydrate | 180 mg |
| | hydroxypropyl cellulose | 30 mg |
| | polyvinylpyrrolidone k-30 | 30 mg |
| | magnesium stearate | 10 mg |
| | carboxymethylcellulose calcium | 20 mg |

Capsules were prepared with the ingredients of the following tables by the conventional manufacturing method.

| | | |
|---|---|---|
| capsule (400 mg) | compound of example 4 | 250 mg |
| | lactose monohydrate | 100 mg |
| | starch | 35 mg |
| | hydroxypropylcellulose | 5 mg |
| | magnesium stearate | 10 mg |

What is claimed is:

1. A compound of general formula (I)

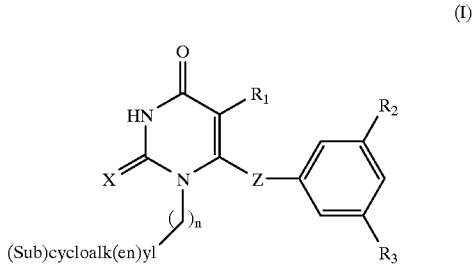

wherein $R_1$, $R_2$, and $R_3$ independently represent hydrogen atom or $C_1$–$C_4$ alkyl, Z represents an oxygen atom, sulfur atom or carbonyl group, X represents an oxygen atom, n represents an integer of 1–3, and (Sub)cycloalk(en)yl represents

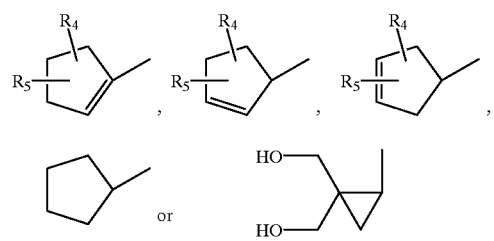

in which $R_4$ and $R_5$ independently represent hydrogen atom, hydroxymethyl, or protected hydroxymethyl with a protecting group selected from trimethylsilyl, dimethylphenylsilyl and t-butyldimethylsilyl; or a pharmaceutically acceptable acid addition salt thereof.

2. A process for the preparation of a compound of general formula (I)

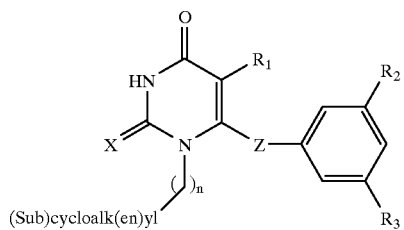

(I)

comprising reacting a compound of formula (a)

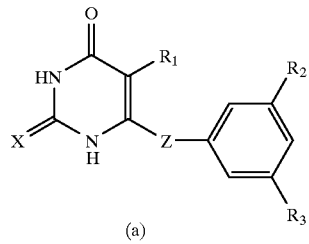

with a compound of formula (b)

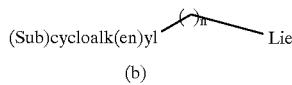

wherein $R_1$, $R_2$, and $R_3$ independently represent hydrogen atoms or $C_1$–$C_4$ alkyl, Z represents an oxygen atom, sulfur atom or carbonyl group, X represents an oxygen atom, n represents an integer of 1–3, (Sub)cycloalk(en)yl represents

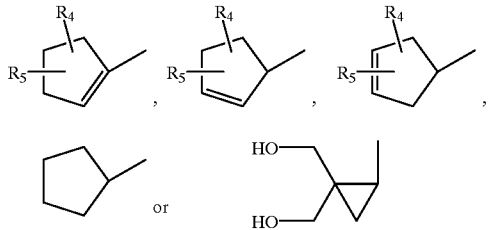

in which $R_4$ and $R_5$ independently represent hydrogen atom, hydroxymethyl, or protected hydroxymethyl with a protecting group selected from trimethylsilyl, dimethylphenylsilyl and t-butyldimethylsilyl; and Lie represents a leaving group selected from halogen atom, methanesulfonyl, para-toluenesulfonyl, benzenesulfonyl and para-nitrobenzenesulfonyl.

3. A pharmaceutical composition comprising a compound of general formula I

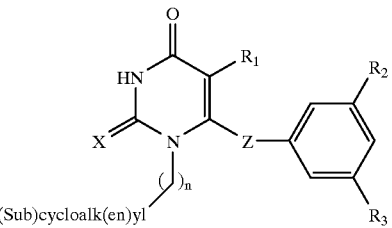

(I)

or a pharmaceutically acceptable acid addition salt thereof as an active ingredient, wherein $R_1$, $R_2$, and $R_3$ independently represent hydrogen atom or $C_1$–$C_4$ alkyl, Z represents an oxygen atom, sulfur atom or carbonyl group, X represents an oxygen atom, n represents an integer of 1–3, and (Sub)cycloalk(en)yl represents

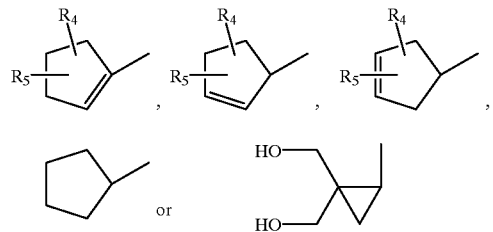

in which $R_4$ and $R_5$ independently represent hydrogen atom, hydroxymethyl, or protected hydroxymethyl with a protecting group selected from trimethylsilyl, dimethylphenylsilyl and t-butyldimethylsilyl; and one or more conventional adjuvants selected from the group consisting of conventional vehicles, binding agents, degrading agents, lubricating agents, dissolving agents, aids for dissolution, stabilizing agents, bases of ointments, pH-adjusting agents and perfumes.

* * * * *